(12) United States Patent
Hopper

(10) Patent No.: US 9,486,353 B2
(45) Date of Patent: Nov. 8, 2016

(54) SPRING-BIASED NASAL MOLDING DEVICE

(71) Applicant: Richard A. Hopper, Seattle, WA (US)

(72) Inventor: Richard A. Hopper, Seattle, WA (US)

(73) Assignee: SEATTLE CHILDREN'S HOSPITAL, Seattle, WA (US)

( * ) Notice: Subject to any disclaimer, the term of this patent is extended or adjusted under 35 U.S.C. 154(b) by 140 days.

(21) Appl. No.: 14/225,934

(22) Filed: Mar. 26, 2014

(65) Prior Publication Data

US 2015/0272770 A1  Oct. 1, 2015

(51) Int. Cl.
*A61F 5/08* (2006.01)
*A61B 17/24* (2006.01)

(52) U.S. Cl.
CPC ........ *A61F 5/08* (2013.01); *A61B 17/24* (2013.01)

(58) Field of Classification Search
CPC ......... A61F 5/08; A61F 5/56; A61B 1/0014; A61B 1/6819; A61B 5/6838; A61B 17/24; A61B 17/12; A61B 2017/12004; Y10T 24/44385; Y10T 24/44462; Y10T 24/4447

USPC ................... 606/199, 156, 157, 204.25, 197; 24/499, 500, 510, 566, 567
See application file for complete search history.

(56) References Cited

U.S. PATENT DOCUMENTS

| 1,069,459 | A | * | 8/1913 | Myles | ........................ | A61F 5/08 606/199 |
| 5,361,459 | A | * | 11/1994 | Hyvonen | ................... | A45F 5/02 224/269 |
| 6,397,439 | B1 | * | 6/2002 | Langford | ................ | D06F 55/00 24/499 |
| 8,323,308 | B2 | * | 12/2012 | Hopper | ................... | A61B 19/24 606/196 |
| 8,523,896 | B2 | | 9/2013 | Hopper | | |

* cited by examiner

*Primary Examiner* — David C Eastwood
*Assistant Examiner* — Mikail Mannan
(74) *Attorney, Agent, or Firm* — Thomas C. Saitta

(57) ABSTRACT

A spring-biased nasal molding device for presurgical molding of cleft lip deformities, the device having a V-shaped spring member joined to a pair of intra-nasal shaping members for insertion in a nostril, and having an extra-nasal shaping member to be positioned external to the nostril connected to each intra-nasal shaping member, wherein the intra-nasal and extra-nasal shaping members are brought together by the spring member to mold the nasal anatomy into the desired shape.

15 Claims, 4 Drawing Sheets

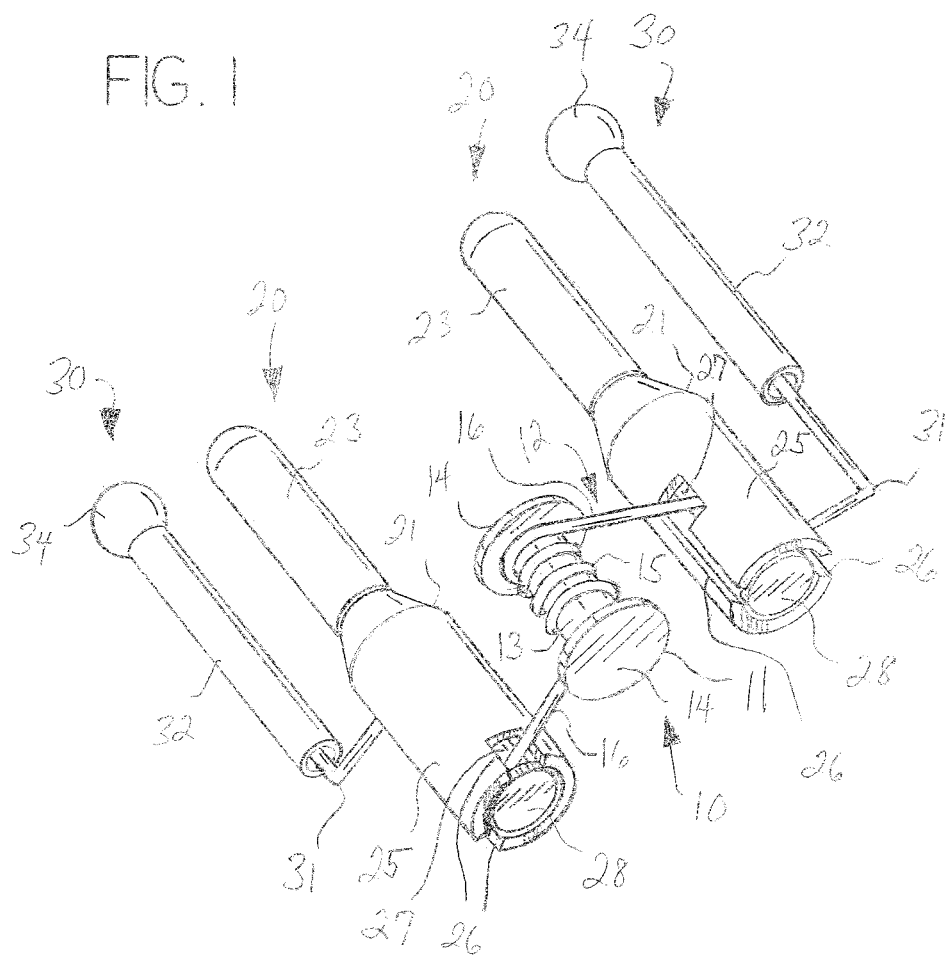

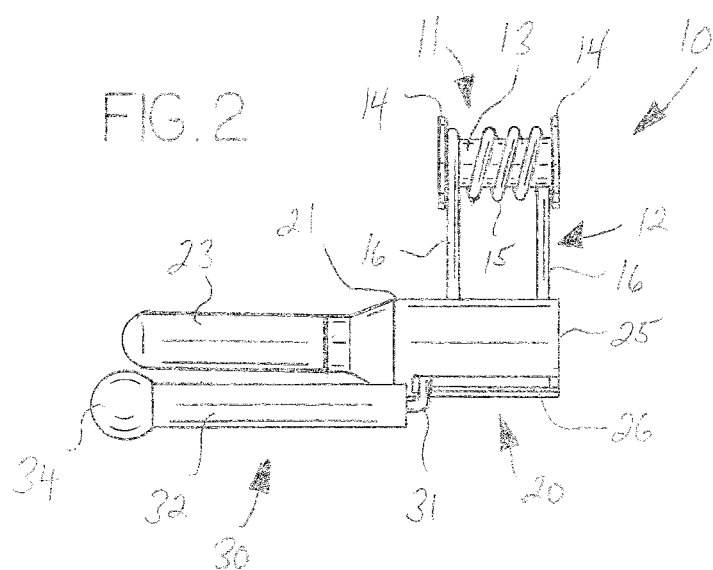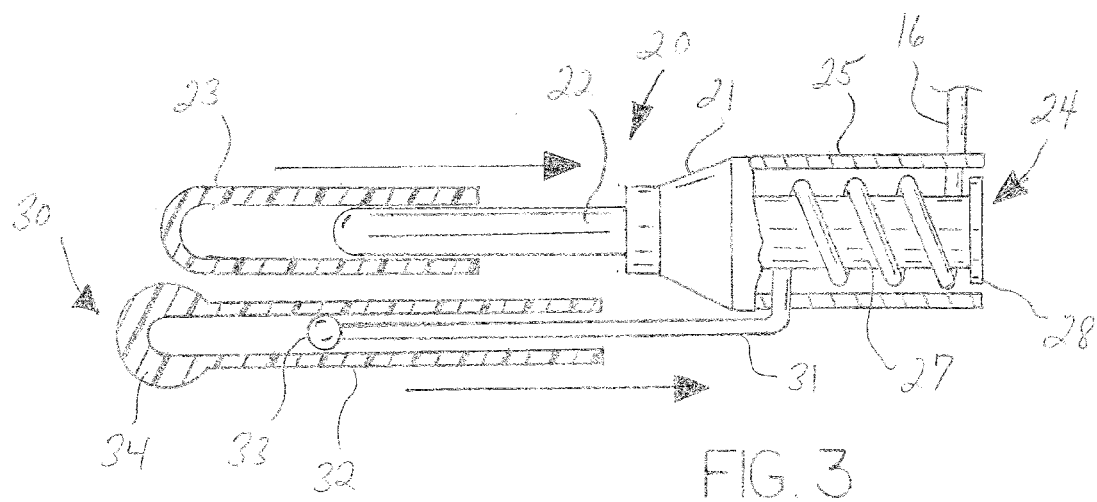

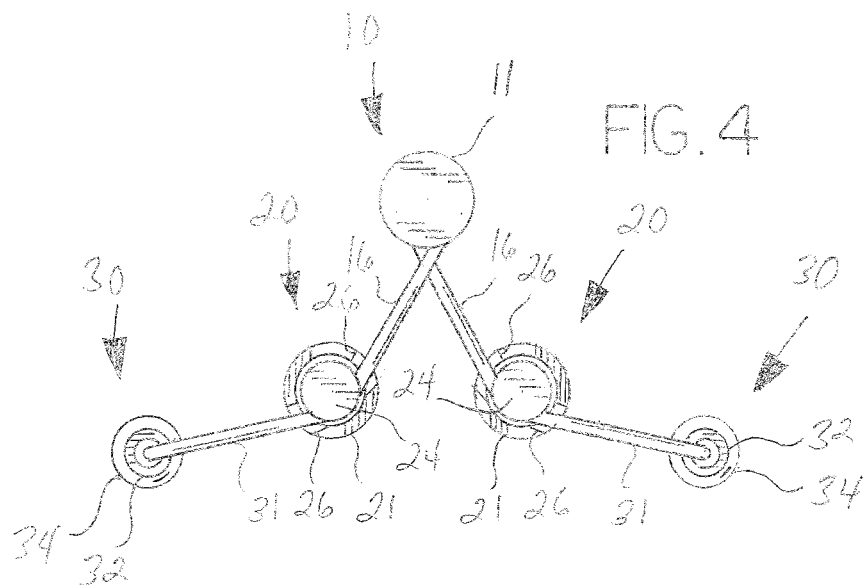
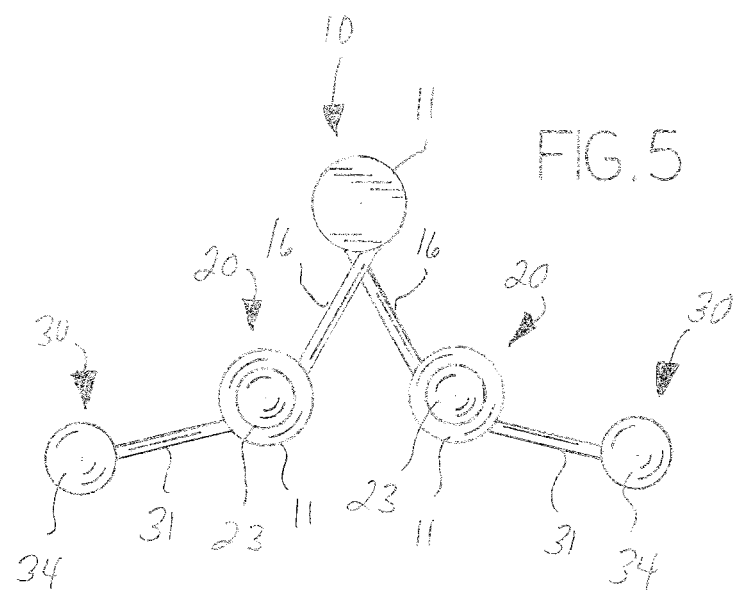

SPRING-BIASED NASAL MOLDING DEVICE

BACKGROUND OF THE INVENTION

This invention relates generally to the field of orthopedic appliances used to presurgically ameliorate congenital cleft lip deformities in infants by the application of direct controlled molding forces, such appliances often referred to as nasoalveolar molding (NAM) appliances, as well as to methods of correcting cleft lips using such NAM appliances.

A key component of the cleft lip deformity is nasal asymmetry and abnormal form. Current surgical techniques can achieve limited correction. Pre-surgical nasal molding has become popular in large cleft centers in an attempt to minimize the nasal deformity prior to surgery. Unlike adult cartilage, the nasal cartilages of an infant are responsive to external molding pressures and will permanently change shape. The most common pre-surgical treatment (nasoalveolar molding) now in use is limited to linear molding changes on the nostrils, and requires an oral splint for stabilization of the nasal molding component. The traditional NAM treatment protocol requires weekly visits to the orthodontist over the first three months of life of the infant for progressive manual adjustment of the NAM device to alter the molding forces on the infant's alveolus and nasal anatomy. The traditional NAM device relies on taping across the base of the nose to achieve medial movement of the lateral crura and alar bases, and a separate pressure post based on an acrylic oral splint to fit inside the nostril and lift the nasal tip. Limitations of this existing technique are that the taping force is extremely variable in achieving the desired result, can distort the upper lip, and since the upward force is more powerful than the taping, an enlarged, iatrogenic triangulated nostril deformity can result.

Improved methodologies and nasal molding devices are disclosed in U.S. Pat. No. 8,323,308 to Hopper and U.S. Pat. No. 8,523,896 to Hopper, in which a dynamic NAM device is disclosed. The device in a main embodiment comprises a pair of rotation assemblies each having an internal shaping member for insertion in a nostril and an external shaping member to be positioned externally to the nostril, wherein the internal and external shaping members are progressively incrementally pivoted about the rotation assemblies, while simultaneously the separation distance between the rotation assemblies is incrementally decreased by reducing the angular separation about a centralized assembly, thereby molding the nasal anatomy into the desired shape over time. The device requires mechanisms to lock the angular positioning of the centralized assembly and the rotational positioning of the external/internal shaping members. Furthermore, the device requires multiple manual adjustments over the course of time.

It is an object of this invention to provide a device and a method that addresses the problems encountered in the known devices and methods for presurgical molding and shaping of anatomical members distorted or improperly formed due to the presence of a cleft lip. It is a further object to provide a spring-biased nasal molding device that imparts a three-dimensional rotational change in nasal morphology in preparation for corrective surgery, which device is self-retaining and self-supporting due to opposing tension across the nose, to rotate the lateral crura and alar crease of the lower lateral cartilages of the nose medially and superiorly, while simultaneously elevating the genu and soft triangle of the nasal tip superiorly, with the simultaneous, coordinated and progressive rotational molding of the nostril width and height precluding nasal aperture distortion or enlargement. It is a further object to provide such a device that automatically and continuously provides the shaping force without need for manual adjustment after placement in the nasal anatomical members.

SUMMARY OF THE INVENTION

A spring-biased nasal molding device is presented that is an orthopedic appliance adapted for automatically and continuously shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The nasal molding device is self-supporting and self-retaining on the patient. The nasal molding device is easily sized and oriented relative to each patient.

The nasal molding device comprises in general a V-shaped spring member, a pair of intra-nasal shaping members connected to the spring member, and a pair of extra-nasal shaping members connected to the intra-nasal shaping members. In use the spring-biased nasal molding device is applied to the patient with the intra-nasal shaping members inserted internally into the nostrils and with the extra-nasal shaping members positioned bilaterally externally to the nostrils along the alar crease between the nasal and cheek units.

In differing embodiments of the invention, the spring member may for example comprise a helical torsion spring or a V-spring bridging the main housing members of the intra-nasal shaping members. A spool-like core member may be positioned within the coiled portion of the helical torsion spring, with bridging segments of the spring extending to the intra-nasal shaping members. The intra-nasal shaping member may comprise an elongated projecting post which retains a cushioned cover member. The extra-nasal shaping members may comprise an L-shaped arm member on which is mounted a cushioned cover member. The L-shaped arm member may comprise the end segments of the spring member extending through the housing members of the intra-nasal shaping members, and the spring member may be coiled about a spool-like internal mounting member disposed in each of the intra-nasal housing members.

With this structure, a properly sized nasal molding device is chosen, the device possessing the desired final separation distance between the intra-nasal shaping members and also possessing the desired spring strength to apply the correct amount of force to the nasal structures. The intra-nasal shaping members are then spread apart by the medical practitioner and placed onto the patient such that the intra-nasal member are inserted into the nostrils and the extra-nasal members are positioned externally to the nostrils. The relationship of the intra-nasal and extra-nasal shaping members in combination with biasing force of the spring member serves to retain the device on the patient without need for additional affixation and serves over time to mold and reposition the anatomical features into the desired configuration.

BRIEF DESCRIPTION OF THE DRAWINGS

FIG. 1 is a perspective view of an embodiment of the invention utilizing a helical torsion spring.

FIG. 2 is a side view of the embodiment of FIG. 1.

FIG. 3 is a partial side view of the embodiment of FIG. 1, shown in partial cross-section and with the cover members FIG. 4 is a rear view of the embodiment of FIG. 1.

FIG. 5 is a front view of the embodiment of FIG. 1.

DETAILED DESCRIPTION OF THE INVENTION

Figure 6:
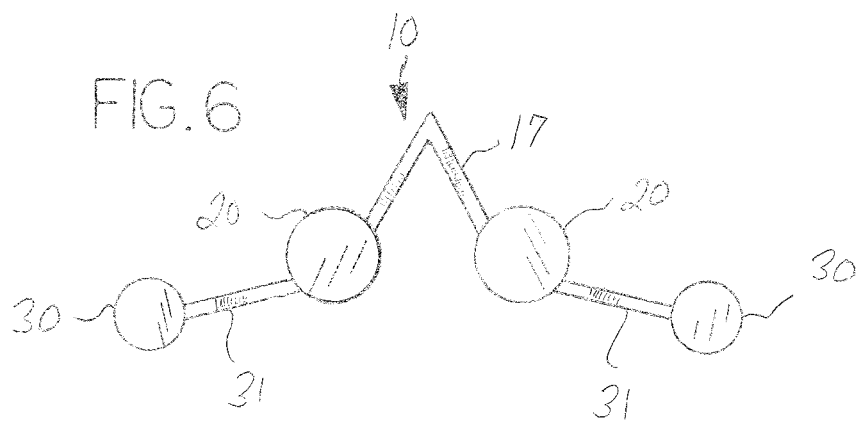
FIG. 6 illustrates an alternative embodiment of the invention utilizing a V-spring.

With reference to the drawings, the spring-biased nasal molding device or appliance will now be described in detail with regard for the best mode and preferred embodiment or embodiments, along with its method of use in correcting cleft lips. In general, the nasal molding device is an orthopedic appliance structured and adapted for shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The nasal molding device is self-supporting and self-retaining on the patient, such that the need for adhesive tape or elastic members to maintain the device on the patient is obviated or greatly minimized. The nasal molding device is easily sized and oriented relative to each patient, and the device applies continuous pressure during the corrective process.

The nasal molding device comprises in a most general sense a centralized spring member 10, a pair of intra-nasal or shaping members 20 connected to the spring member 10, and a pair of extra-nasal shaping members 30 connected to the intra-nasal shaping members 20. In use the nasal molding device is applied to the patient with the intra-nasal shaping members 20 inserted into the nostrils and with the extra-nasal shaping members 30 positioned bilaterally along the alar crease between the nasal and cheek units.

The spring member 10 is a V-shaped biasing mechanism that pulls the intra-nasal shaping members 20 toward each other, preferably over an arced pathway. The spring member 10 may comprise for example a helical torsion spring or a V-spring. The embodiment shown in FIGS. 1, 2, 4 and 5 comprises a helical torsion spring 12 having a coil segment 15 and a pair of bridging segments 16 extending radially outward from the central axis of the coil segment 15 to form a V-shaped configuration, each bridging segment 16 being attached to an intra-nasal shaping member 20. In a preferred embodiment, a core member 11 may be disposed within the coiled segment 15 of the helical torsion spring 12, and the core member 11 may comprise a cylindrical body 13 with a pair of radially extending rim members 14, such that the core member 11 is spool-shaped.

Alternatively, spring member 10 may comprise a V-spring 18 formed of wire or flat bar, the V-spring 18 oriented in an inverted position such that the angle of the "V" points upward when the device is utilized on a patient and such that the ends of the "V" are attached to the intra-nasal shaping members 20, as shown in FIG. 6.

Figure 7:
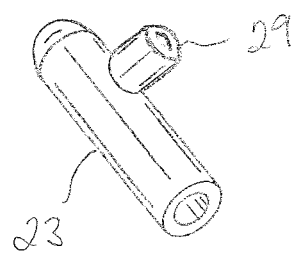
FIG. 7 illustrates an alternative embodiment for the intra-nasal cover member.

Two intra-nasal shaping members 20 are connected to spring member 10 so as to extend rearward and into the nostril cavity when the device is applied to the patient. The intra-nasal shaping members 20 are adapted to have contact with the nasal lining directly on the undersurface of the lower lateral cartilages from the top of the ascending limb, along the genu to the lateral crus, but to have minimal contact with the alar rim. The intra-nasal shaping members 20 each comprise a generally rigid projecting post 22 on which is mounted a cover member 23 preferably composed of a compressible or less rigid material such as a silicone or similar polymer. The cover members 23 are preferably removable, as illustrated in FIG. 3 and may be of differing thicknesses or configurations to better size the internal shaping member 20 to the patient and to provide a desired lifting and molding surface, as shown in FIG. 7, where the cover member 23 is provided with a lateral molding member 29. This lateral molding member 29 is oriented to the side when the extra-nasal shaping members 30 are rotated inwards, but as the molding force rotates the extra-nasal shaping members 30 outwards (i.e. counterclockwise for the left extra-nasal shaping member 30 and clockwise for the right extra-nasal shaping member 30) the lateral molding members 29 rotate upward to lift the nostrils. In a typical procedure, three embodiments of the cover member 23 will be utilized—one with no lateral molding member 29, one with a small lateral molding member 29 and the other with a large lateral molding member 29. In a preferred embodiment shown in FIGS. 1 through 5, the intra-nasal shaping member 20 comprises a main housing 21 of greater diameter than the projecting post 22.

An extra-nasal shaping member 30 is mounted onto each intra-nasal member 20 in a manner whereby the extra-nasal shaping members 30 are positioned outwardly or laterally to said intra-nasal shaping members 20, and such that the extra-nasal shaping members 30 and the intra-nasal shaping members 20 are substantially in parallel, as shown in FIGS. 4 and 5. Each extra-nasal shaping member 30 is positioned so as to contact the skin of the alar crease at the lateral aspect of the nose and thus provide opposing contact to the lateral crus contact of the intra-nasal shaping member 20. The extra-nasal shaping member 30 is mounted to the intra-nasal shaping member 20 by an arm member 31, which may be L-shaped such that a short portion of the arm member 31 extends laterally from the intra-nasal shaping member 20 and a longer portion extends rearward to form the main body of the extra-nasal shaping member 30. A cover member 32 may be provided on the arm member 31, the cover member 32 preferably being composed of a compressible or less rigid material such as a silicone or similar polymer. The cover members 32 are preferably removable, as illustrated in FIG. 3 and may be of differing thicknesses or configurations to better size the extra-nasal shaping member 30 to the patient. The arm member 31 may be provided with a retaining knob 33 and the cover member 32 may be provided with a cushioning head 34, as shown in FIG. 3.

The spring member 10 may be affixed directly to the exterior or interior of each main housing 21, and in a preferred embodiment the main housing 21 comprises a tubular portion 25, the bridging segments 16 of helical torsion spring 12 extending through slots 26 into the interior of the tubular portion 25. The bridging segment 16 is then coiled around an internal mounting member 24. The arm members 31 connecting the extra-nasal shaping members 30 to the intra-nasal shaping members 20 may be externally or internally connected to the intra-nasal shaping members 20, and may be rigid, spring-like or malleable. In a preferred embodiment shown best in FIG. 3, the helical torsion spring 12 is extended outwardly from each intra-nasal shaping member 20 through a slot 26 such that arm members 31 are formed from a portion of the helical torsion spring 12. The slots 26 must be of sufficient width circumferentially to allow the intra-nasal shaping members 20 to rotate independently of any central widening.

The intra-nasal shaping members 20 and the extra-nasal shaping members 30 are sized and configured so as to occupy a relatively small volume within the nasal cavity to minimize interference with breathing. The initial positioning of the extra-nasal shaping members 30 relative to the intra-nasal shaping members 20 is determined by the anatomy of the patient and whether a single or bilateral deformity is presented, and may be adjusted by bending the arm members 31. To utilize the device, the spring member 10 is manually flexed by spreading apart the intra-nasal shaping members 20, thereby loading spring member 10. The intra-nasal shaping members 20 are then inserted into the nostrils and the extra-nasal members 30 are positioned externally to the nostrils. The biasing force of the spring member 10 then imparts a continuous force pulling the intra-nasal shaping members 20, the extra-nasal shaping members 30 and the patient's anatomical features together along an arced pathway in the corrective direction, which serves over time to mold and reposition the anatomical features into the desired configuration for further medical procedures.

It is contemplated that certain equivalents or substations for elements set forth above may be obvious to those of ordinary skill in the art, and therefore the true scope and definition of the invention is to be as set forth in the following claims.

I claim:

1. A nasal molding device adapted for pre-surgical molding of cleft lip deformities in a patient, said device comprising: two intra-nasal shaping members;
   a spring member connecting said intra-nasal shaping members, said spring member having a V-shaped configuration;
   an extra-nasal shaping member connected to each of said intra-nasal shaping members; wherein said intra-nasal shaping members are adapted to be positioned in the nostrils of the patient having a cleft lip deformity and said extra-nasal shaping members are adapted to be positioned along the alar creases of the patient, such that the tissue of the patient is retained between the intra-nasal shaping members and the extra-nasal shaping, and
   whereby said intra-nasal shaping members are separable by manually flexing said spring member, and whereby upon release said spring member brings said intra-nasal shaping members together over an arced pathway;
   wherein said intra-nasal shaping members each comprise a main housing having a tubular portion, two slots and an internal mounting member, wherein said spring member extends into said housing member through one of said slots, coils around said internal mounting member and extends out of said housing member through the other of said slots.

2. The device of claim 1, wherein said spring member is a helical torsion spring.

3. The device of claim 1, wherein said spring member is a V-spring.

4. The device of claim 1, wherein said spring member extends through said intra-nasal shaping members and connects said extra-nasal shaping members to said intra-nasal shaping members.

5. The device of claim 1, wherein said intra-nasal shaping members each comprises a projecting post and a cover member disposed on said projecting post.

6. The device of claim 5, wherein said extra-nasal shaping members each comprises an L-shaped arm member and a cover member disposed on said arm member.

7. The device of claim 1, wherein said extra-nasal shaping members each comprises an L-shaped arm member and a cover member disposed on said arm member.

8. The device of claim 1, wherein said intra-nasal shaping members and said extra-nasal shaping members are positioned substantially parallel to each other.

9. The apparatus of claim 1, said extra-nasal shaping members being connected to said intra-nasal shaping members such that each said extra-nasal shaping member moves in the same direction as the intra-nasal shaping member to which it is connected; and
   whereby upon release said spring member brings said extra-nasal shaping members together over an arced pathway.

10. A nasal molding device adapted for pre-surgical molding of cleft lip deformities in a patient, said device comprising:
    two intra-nasal shaping members each comprising a projecting post and a cover member disposed on said projecting post;
    a spring member connecting said intra-nasal shaping members, said spring member having a V-shaped configuration;
    an extra-nasal shaping member connected to each of said intra-nasal shaping members, each said extra-nasal shaping member comprising an L-shaped arm member and a cover member disposed on said arm member;
    wherein said intra-nasal shaping members and said extra-nasal shaping members are positioned substantially parallel to each other;
    wherein said intra-nasal shaping members are adapted to be positioned in the nostrils of the patient having a cleft lip deformity and said extra-nasal shaping members are adapted to be positioned along the alar creases of the patient, such that the tissue of the patient is retained between the intra-nasal shaping members and the extra-nasal shaping, and
    whereby said intra-nasal shaping members are separable by manually flexing said spring member, and whereby upon release said spring member brings said intra-nasal shaping members together over an arced path;
    wherein said intra-nasal shaping members each comprise a main housing having a tubular portion, two slots and an internal mounting member, wherein said spring member extends into said housing member through one of said slots, coils around said internal mounting member and extends out of said housing member through the other of said slots.

11. The device of claim 10, wherein said spring member extends through said intra-nasal shaping members and connects said extra-nasal shaping members to said intra-nasal shaping members.

12. The device of claim 11, wherein said spring member is a helical torsion spring.

13. The apparatus of claim 10, said extra-nasal shaping members being connected to said intra-nasal shaping members such that each said extra-nasal shaping member moves in the same direction as the intra-nasal shaping member to which it is connected; and
    whereby upon release said spring member brings said extra-nasal shaping members together over an arced pathway.

14. A method of pre-surgically molding a cleft lip deformity in a patient comprising the steps of:
    providing the device of claim 1;
    manually flexing said spring member to separate said intra-nasal shaping members, inserting said intra-nasal shaping members into the nostrils of said patient and positioning said extra-nasal shaping members along the alar creases of said patient such that tissue of said patient is between said intra-nasal shaping members and said extra-nasal shaping members; and releasing said spring member.

15. The method of claim 14, wherein said step of releasing said spring member brings said intra-nasal shaping members together along an arced pathway and brings said extra-nasal shaping members together along an arced pathway.

* * * * *